US009585896B2

(12) United States Patent
Fraser et al.

(10) Patent No.: US 9,585,896 B2
(45) Date of Patent: *Mar. 7, 2017

(54) COMPOSITIONS COMPRISING OMEGA-3 FATTY ACIDS AND VITAMIN D FOR PSORIASIS, AND METHODS AND USES THEREOF

(71) Applicant: PRONOVA BIOPHARMA NORGE AS, Lysaker (NO)

(72) Inventors: David A Fraser, Oslo (NO); Alexis Garras, Oslo (NO)

(73) Assignee: PRONOVA BIOPHARMA NORGE AS, Lysaker (NO)

( * ) Notice: Subject to any disclaimer, the term of this patent is extended or adjusted under 35 U.S.C. 154(b) by 0 days.

This patent is subject to a terminal disclaimer.

(21) Appl. No.: 14/390,127

(22) PCT Filed: Mar. 15, 2013

(86) PCT No.: PCT/IB2013/001214
§ 371 (c)(1),
(2) Date: Oct. 2, 2014

(87) PCT Pub. No.: WO2013/150384
PCT Pub. Date: Oct. 10, 2013

(65) Prior Publication Data
US 2015/0056276 A1  Feb. 26, 2015

Related U.S. Application Data

(60) Provisional application No. 61/620,263, filed on Apr. 4, 2012.

(51) Int. Cl.
| | | |
|---|---|---|
| *A61K 31/59* | (2006.01) | |
| *A61K 31/593* | (2006.01) | |
| *A61K 31/202* | (2006.01) | |

(52) U.S. Cl.
CPC ............ *A61K 31/593* (2013.01); *A23L 33/12* (2016.08); *A23L 33/155* (2016.08); *A61K 31/202* (2013.01); *A23V 2002/00* (2013.01)

(58) Field of Classification Search
USPC ........................................................ 514/167
See application file for complete search history.

(56) References Cited

U.S. PATENT DOCUMENTS

| | | | |
|---|---|---|---|
| 4,652,441 A | 3/1987 | Okada et al. | |
| 5,445,832 A | 8/1995 | Orsolini et al. | |
| 6,245,811 B1 | 6/2001 | Horrobin et al. | |
| 8,652,508 B2* | 2/2014 | Puder et al. | 424/439 |
| 2004/0254357 A1 | 12/2004 | Zaloga et al. | |
| 2005/0074443 A1 | 4/2005 | Treadwell | |
| 2011/0165291 A1* | 7/2011 | Loblaw et al. | 426/73 |

FOREIGN PATENT DOCUMENTS

| | | |
|---|---|---|
| EP | 0052510 | 8/1986 |
| ES | 2009346 | 9/1989 |
| GB | 1393805 | 5/1975 |
| GB | 2209937 | 6/1988 |
| WO | WO 03/084516 | 10/2003 |
| WO | WO 2004/064716 A2 | 8/2004 |
| WO | WO 2005/105071 A1 | 11/2005 |
| WO | WO 2006/000229 | 1/2006 |
| WO | WO 2012/032417 A2 | 3/2012 |
| WO | WO 2012/075093 A2 | 6/2012 |

OTHER PUBLICATIONS

All in One Omega 3,5,6,7 & 9 with Vitamin D3 by Puritan's Pride, 2010.*
Mega EFA-D3 Omega-3 EPA & DHA by Vitacost, 2010.*
Lalvani et al. CAS: 151: 366739, 2009.*
Manson et al., Contemporary, Oct. 2, 2011, 33( ): 159-171.*
Morimoto et alo., British Journal of Dermatology, 1986, 115:421-429.*
Mayser et al., Journal American Acad. Dermatol, 1998, 38(4):539-47.*
Simopoulos, J Am Coll Nutr, 2002, 21(6):495-505.*
Soyland et al., Eur J. Clin Invest, 1994, 24(4):236-42.*
Okano, Int J. Dermatol, 1991, 30(1):62-4.*
Bittiner, S.B. et al., "A Double-Blind Randomized Placebo-Controlled Trial of Fish Oil in Psoriasis," *Lancet*, vol. 1, No. 8582, pp. 378-380 (1988).
Demchenko, D.V. et al, "Validated HPTLC Method for Quantification of Vitamin D-3 in Fish Oil," *Journal of Planar Chromatography*, vol. 24, No. 6, pp. 487-490 (2011).
Halade, G.V. et al., "Docosahexaenoic Acid-Enriched Fish Oil Attenuates Kidney Disease and Prolongs Median and Maximal Life Span of Autoimmune Lupus-Prone Mice," The Journal of Immunology, vol. 184, No. 9, pp. 5280-5286 (2010).
Perez, A. et al., "Safety and Efficacy of Oral Calcitriol (1,25-dihydroxyvitamin D3) for the Treatment of Psoriasis," *British J. Derm.*, vol. 134, No. 6, pp. 1070-1078 (1996).
International Search Report PCT/IB2013/001214, dated Sep. 20, 2013.
International Preliminary Report on Patentability of International Patent Application No. PCT/IB2013/001214, dated Oct. 7, 2014.
Soyland et al., "Effect of dietary supplementation with very-long-chain n-3 fatty acids in patients with psoriasis," *N. Engl. J. Med.*, 328(25):1812-1816 (1993).
Francis, F. J. "Gelatin," Wiley Encyclopedia of Food Science and Technology, 2nd ed.: John Wiley & Sons (1999).

* cited by examiner

*Primary Examiner* — Rei-Tsang Shiao
(74) *Attorney, Agent, or Firm* — Finnegan, Henderson, Farabow, Garrett & Dunner, L.L.P.

(57) ABSTRACT

The present disclosure relates to pharmaceutical compositions comprising omega-3 fatty acids and vitamin D for use in at least one of preventing and treating psoriasis, and to food supplement, dietary supplement, nutritional supplement, over-the-counter (OTC) supplement, medical food, or pharmaceutical grade supplement compositions comprising omega-3 fatty acids and vitamin D for use in improving at least one parameter associated with psoriasis.

11 Claims, No Drawings

COMPOSITIONS COMPRISING OMEGA-3 FATTY ACIDS AND VITAMIN D FOR PSORIASIS, AND METHODS AND USES THEREOF

This application is a National Stage application based on International Patent Application No. PCT/IB2013/001214 filed on Mar. 15, 2013, and claims priority to U.S. Provisional Application No. 61/620,263, filed Apr. 4, 2012, each is incorporated herein by reference in its entirety.

The present disclosure relates generally to pharmaceutical compositions comprising omega-3 fatty acids and vitamin D for use in at least one of preventing and treating psoriasis. Furthermore it relates to a food supplement, dietary supplement, nutritional supplement, over-the-counter (OTC) supplement, medical food, or pharmaceutical grade supplement composition comprising omega-3 fatty acids and vitamin D for use in improving at least one parameter associated, e.g., side effects, with psoriasis.

Psoriasis is an autoimmune disease that appears on the skin. It occurs when the immune system mistakes the skin cells as a pathogen, and sends out faulty signals that speed up the growth cycle of skin cells. Psoriasis is not contagious. It has been linked, however, to an increased risk of stroke. There are five types of psoriasis: plaque, guttate, inverse, pustular and erythrodermic. The most common form, plaque psoriasis, is commonly seen as red and white hues of scaly patches appearing on the top, first layer of the epidermis (skin). Some patients, though, have no dermatological symptoms.

Topical Agents

Bath solutions and moisturizers, mineral oil, and petroleum jelly may help soothe affected skin and reduce the dryness which accompanies the build-up of skin on psoriatic plaques. Medicated creams and ointments applied directly to psoriatic plaques can help reduce inflammation, remove built-up scale, reduce skin turn over, and clear affected skin of plaques. Ointment and creams containing coal tar, dithranol (anthralin), corticosteroids like desoximetasone (Topicort), fluocinonide, vitamin $D_3$ analogues (for example, calcipotriol), and retinoids are routinely used. Generally, topical agents help to normalize skin cell production and reduce inflammation. Activated vitamin D and its analogues can inhibit skin cell proliferation.

Phototherapy

Phototherapy in the form of sunlight has long been used effectively for treatment. Wavelengths of 311-313 nm are effective, and special lamps have been developed for this application. The amount of light used is determined by a person's skin type. Increased rates of cancer from treatment appear to be small.

Psoralen and ultraviolet A phototherapy (PUVA) combines the oral or topical administration of psoralen with exposure to ultraviolet A (UVA) light. Although the mechanism of action of PUVA is unknown, it may involve the activation of psoralen by UVA light, which inhibits the abnormally rapid production of the cells in psoriatic skin. There are multiple mechanisms of action associated with PUVA, including effects on the skin immune system.

Common PUVA treatment side effects include nausea, headache, fatigue, burning, and itching. Long-term treatment can be associated with squamous cell carcinoma (but not with melanoma).

Systemic Agents

Psoriasis that is resistant to topical treatment and phototherapy is typically treated by medications taken internally by pill or injection ("systemic"). Patients undergoing systemic treatment are required to have regular blood and liver function tests because of the toxicity of the medication. Pregnancy must be avoided for the majority of these treatments. Most people experience a recurrence of psoriasis after systemic treatment is discontinued.

The three main traditional systemic treatments include methotrexate, cyclosporine, and retinoids. Methotrexate and cyclosporine are immunosuppressant drugs; retinoids are synthetic forms of vitamin A. Patients taking methotrexate are prone to ulcerations. Methotrexate exposure may also contribute to post-surgical events.

Biologics are another systemic treatment for psoriasis. Biologics are manufactured proteins that interrupt the immune process involved in psoriasis. Unlike generalized immunosuppressant therapies such as methotrexate, biologics focus on specific aspects of the immune function leading to psoriasis. These drugs (interleukin antagonists) are relatively new, and their long-term impact on immune function is unknown, but they have proven effective in treating psoriasis and psoriatic arthritis. Biologics are usually given by self-injection or in a doctor's office. In the United Kingdom in 2005, the British Association of Dermatologists (BAD) published guidelines for use of biological interventions in psoriasis. A UK national register called the BAD Biological Register (BADBIR) has been set up to collect valuable information on side effects and benefits and will be used to inform doctors on how best to use biological agents and similar drugs.

Two biologic drugs that target T cells are efalizumab and alefacept. Efalizumab is a monoclonal antibody which blocks the molecules that dendritic cells use to communicate with T cells. It also blocks the adhesion molecules on the endothelial cells that line blood vessels, which attract T cells. Efalizumab, however, suppresses the immune system's ability to control normally harmless viruses, which may lead to fatal brain infections. Efalizumab was voluntarily withdrawn from the U.S. market in April 2009 by the manufacturer. Alefacept also blocks the molecules that dendritic cells use to communicate with T cells and even causes natural killer cells to kill T cells as a way of controlling inflammation.

Several monoclonal antibodies (MAbs) target cytokines, the molecules that cells use to send inflammatory signals to each other. TNF-α is one of the main executor inflammatory cytokines. Four MAbs (infliximab, adalimumab, golimumab and certolizumab pegol) and one recombinant TNF-α decoy receptor, etanercept, have been developed against TNF-α to inhibit TNF-α signaling. Additional monoclonal antibodies have been developed against pro-inflammatory cytokines IL-12/IL-23 and Interleukin-17 and inhibit the inflammatory pathway at a different point than the anti-TNF-α antibodies. IL-12 and IL-23 share a common domain, p40, which is the target of the recently FDA-approved ustekinumab. Ustekinumab (IL-12/IL-23 blocker) was shown to have higher efficacy than high-dose etanercept over a 12-week period in patients with psoriasis.

In 2008, the FDA approved three new treatment options available to psoriasis patients: 1) Taclonex Scalp, a new topical ointment for treating scalp psoriasis; 2) the Xtrac Velocity excimer laser system, which emits a high-intensity beam of ultraviolet light and can treat moderate to severe psoriasis; and 3) the biologic drug adalimumab (brand name Humira), which was also approved to treat moderate to severe psoriasis. Adalimumab had already been approved to treat psoriatic arthritis. The most recent biologic drug approved to treat moderate to severe psoriasis, as of 2010, is ustekinumab (brand name Stelara).

Medications with the least potential for adverse reactions are generally employed first. If the treatment goal is not achieved, then therapies with greater potential toxicity may be used. Medications with significant toxicity are reserved for severe unresponsive psoriasis. This is called the psoriasis treatment ladder. As a first step, medicated ointments or creams, i.e., topical agents, are applied to the skin. If topical treatment fails to achieve the desired goal, then the second step is to expose the skin to ultraviolet (UV) radiation, i.e., phototherapy. The third step involves the use of medications which are taken internally by pill or injection, i.e., systemic treatment.

A 2010 meta-analysis compares the change in Psoriasis Area and Severity Index (PASI) improvement from baseline in 22 trials. The combination therapy for moderate to severe psoriasis using psoralen with ultraviolet A (PUVA) plus acitretin shows a 97.3% PASI improvement from baseline. Therapy limitations need to be taken into consideration in the treatment of moderate to severe psoriasis, such as the increased risk of skin cancer with phototherapy and birth defects with acitretin.

Alternative Therapy

Some studies suggest psoriasis symptoms can be relieved by changes in diet and lifestyle. Fasting periods, low energy diets, and vegetarian diets have improved psoriasis symptoms in some studies, and diets supplemented with cod liver oil have also shown beneficial effects. Fish oils are rich in two omega-3 fatty acids, eicosapentaenoic acid (EPA) and docosahexaenoic acid (DHA), and contain Vitamin E. Furthermore, cod liver oil contains Vitamin A and Vitamin D.

The severity of psoriasis symptoms may also be influenced by lifestyle habits related to alcohol, smoking, weight, sleep, stress, and exercise.

Another alternative therapy is cannabis. Cannabis might treat psoriasis, due to the anti-inflammatory properties of its cannabinoids, and their regulatory effects on the immune system. The adverse effects of cannabis might be avoided with a topical preparation or by the use of at least one more specific endocannabinoid receptor agonist.

Mode of Action of Psoriasis

The immunopathogenesis of psoriasis involves elements of both the innate and adaptive immune systems, and is characterized by abnormal keratinocyte differentiation and proliferation. Immune cell-derived signals, such as proinflammatory cytokines, stimulate keratinocyte proliferation, which in turn may modulate immune cells through surface and secretory molecules. These molecules consist of toll-like receptors (TLRs), antimicrobial peptides (AMPs), peroxisome proliferator-activated receptors (PPARs), and the active metabolite of vitamin D, $1,25(OH)_2D_3$.

PPAR-$\alpha$ and vitamin D receptor (VDR) are nuclear transcription factors highly expressed on skin and immune cells. After ligand binding, both VDR and PPAR-$\alpha$ signalling pathways regulate genes coordinating multiple cellular functions known to play a central role in the pathogenesis of psoriasis, including cell proliferation, cell differentiation, and innate immune responses. Naturally occurring ligands for PPAR are long-chain omega-3 fatty acids (such as eicosapentaenoic and docosahexaenoic acid), while $1,25(OH)_2D_3$ mediates the effects of vitamin $D_3$ (cholecaliferol) via VDR after intracellular hydroxylation.

Although each receptor exerts differential effects upon gene expression, both VDR and PPAR-$\alpha$ ligands have been shown to have immunomodulatory/anti-inflammatory and anti-proliferative effects upon cells involved in the formation of psoriatic lesions, such as keratinocytes, langerhans cells and T-lymphocytes. VDR and PPAR-$\alpha$ therefore represent major targets for the treatment of many inflammatory skin diseases, including psoriasis. Furthermore, due to differential yet overlapping effects upon gene expression, simultaneous activation of PPAR-$\alpha$, and VDR signaling pathways may offer great benefit in the treatment and maintenance of remission of psoriasis.

Decreased expression of both PPAR-$\alpha$ and VDR has been found in psoriatic lesions and VDR expression is decreased even further in psoriatic lesions of vitamin D-deficient, as compared to vitamin D-sufficient, patients. Furthermore, the cellular manifestations of decreased expression of both VDR and PPAR-$\alpha$ may be exacerbated by the fact that both nuclear receptors compete to heterodimerize with retinoic acid receptor (RXR). Heterodimerization of VDR and PPAR-$\alpha$ to RXR is a required step before binding of VDR/RXR or PPAR-$\alpha$/RXR to DNA and gene transcription can occur. Despite their established anti-inflammatory and anti-proliferative effects, monotherapy with high concentrations of PPAR ligands, such as omega-3 fatty acids, may therefore have limited efficacy in psoriasis if (a) there is low expression of PPAR-$\alpha$, (b) increased PPAR-$\alpha$ ligand binding, and/or (c) PPAR-$\alpha$/RXR heterodimer formation further decreases VDR/RXR heterodimer formation either with or without the presence of suboptimal plasma vitamin D concentrations. As such it was previously shown by Soyland et al. in a double-blind placebo controlled study that monotherapy with high-doses of omega-3 fatty acids during winter months was ineffective in psoriatic patients living in northern latitudes where vitamin D deficiency (25-hydroxyvitamin D [25(OH)D]) concentrations <20 μg/mL) is prevalent (i.e. Soyland et al., "Effect of dietary supplementation with very-long-chain n-3 fatty acids in patients with psoriasis," N Engl J. Med. 1993 Jun. 24, 328(25):1812-6).

It is known that both EPA and DHA and/or their oxygenated derivatives are PPAR-$\alpha$ ligands. EPA and DHA thus serve as PPAR-$\alpha$ ligands which, as described above, have anti-inflammatory and immunomodulatory effects upon activated keratinocytes and T-cells.

DHA has been shown in vivo to be superior to EPA for reducing LPS-mediated PI3K, Akt, and NF-kappaB activation, and importantly IL-18 induction and IL-18 signaling in the autoimmune prone (NZB×NZW)F1 (B×W) mice (see Halade G V et al., "Docosahexaenoic acid-enriched fish oil attenuates kidney disease and prolongs median and maximal life span of autoimmune lupus-prone mice," J. Immunol. 2010 May 1, 184(9):5280-6).

SUMMARY

The current disclosure concerns prevention and treatment of psoriasis by administration of a composition comprising a fatty acid oil mixture and Vitamin D. In at least one embodiment, at least one of prevention and treatment of psoriasis is effected in patients already on treatment—as described above—by administration of a composition comprising omega-3 fatty acids and Vitamin D.

An optimal combination of vitamin D and omega-3 fatty acids may synergistically inhibit the proliferative/pro-inflammatory activity of key cells involved in the generation of psoriatic lesions (CD4+ T-cells and keratinocytes). Therefore, the combination of vitamin D and omega-3 fatty acids may be utilized in the treatment of established psoriasis.

Thus, the present disclosure is directed to a pharmaceutical composition comprising omega-3 fatty aids and vitamin D for use in at least one of preventing and treating psoriasis.

The present inventors have found that a combination of high-concentrated DHA and Vitamin D₃ provides beneficial effects in prevention and/or treatment of psoriasis.

The present disclosure is also directed to a method for at least one of preventing and treating psoriasis in a subject in need thereof comprising administering to the subject in need thereof a pharmaceutical composition comprising omega-3 fatty acids and vitamin D.

The present disclosure is further directed to a food supplement, dietary supplement, over the counter (OTC) supplement, medical food or nutritional supplement, including pharmaceutical grade, composition comprising omega-3 fatty acids and vitamin D is provided. Such a supplement composition may be useful in decreasing skin flaking and itching associated with psoriasis. It may also help to improve dry skin conditions such as, for example, skin dryness, dry skin aspects, skin comfort, skin soothing, and/or signs of skin ageing.

Additionally, the present disclosure is directed to a method for improving at least one parameter, e.g. side effects, associated with psoriasis in a subject in need thereof, comprising administering to the subject in need thereof a food supplement, dietary supplement, over the counter (OTC) supplement, medical food, nutritional supplement, or pharmaceutical grade supplement composition comprising omega-3 fatty acids and vitamin D. The improvement in at least one parameter may be chosen from decreasing skin flaking and itching associated with psoriasis and improving dry skin conditions such as, for example, skin dryness, dry skin aspects, skin comfort, skin soothing, and/or signs of skin aging.

DESCRIPTION

The present disclosure is directed to a pharmaceutical composition for psoriasis comprising: a fatty acid oil mixture comprising at least 75% of at least one fatty acid chosen from eicosapentaenoic acid (EPA) and docosahexaenoic acid (DHA), by weight of the fatty acid oil mixture, wherein the EPA and DHA are in a form chosen from methyl or ethyl ester, triglyceride and free fatty acid; and vitamin D.

The present disclosure is further directed to a method for at least one of preventing and treating psoriasis in a subject in need thereof comprising administering to the subject in need thereof a pharmaceutical composition comprising: a fatty acid oil mixture comprising at least 75% of at least one fatty acid chosen from eicosapentaenoic acid (EPA) and docosahexaenoic acid (DHA), by weight of the fatty acid oil mixture, wherein the EPA and DHA are in a form chosen from ethyl ester, triglyceride and free fatty acid; and vitamin D.

The present disclosure is also directed to a food supplement, dietary supplement, over the counter (OTC) supplement, medical food, nutritional supplement, or pharmaceutical grade supplement composition for improvement of at least one parameter associated with psoriasis comprising: a fatty acid oil mixture comprising from about 25% to about 100% of at least one fatty acid chosen from eicosapentaenoic acid (EPA) and docosahexaenoic acid (DHA), by weight of the fatty acid oil mixture, wherein the EPA and DHA are in a form chosen from ethyl ester, triglyceride, and free fatty acid; and vitamin D.

The present disclosure is further directed to a method for improving at least one parameter associated with psoriasis in a subject in need thereof comprising administering to the subject a food supplement, nutritional supplement, dietary supplement, over the counter (OTC) supplement, medical food, or pharmaceutical grade supplement composition comprising: a fatty acid oil mixture comprising from about 25% to about 100% of at least one fatty acid chosen from eicosapentaenoic acid (EPA) and docosahexaenoic acid (DHA), by weight of the fatty acid oil mixture, wherein the EPA and DHA are in a form chosen from ethyl ester, triglyceride and free fatty acid; and vitamin D.

Particular aspects of the disclosure are described in greater detail below. The terms and definitions as used in the present application and as clarified herein are intended to represent the meaning within the present disclosure. The patent and scientific literature referred to herein and referenced above is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±10% of a specified amount, frequency, or value.

The terms "administer," "administration" or "administering" as used herein refer to (1) providing, giving, dosing and/or prescribing by either a health practitioner or his authorized agent or under his direction a composition according to the disclosure, and (2) putting into, taking or consuming by the patient or person himself or herself, a composition according to the disclosure.

Fatty Acid Oil Mixture and Omega-3 Fatty Acids

Compositions of the present disclosure comprise at least one fatty acid oil mixture. The fatty acid oil mixture comprises at least one fatty acid chosen from eicosapentaenoic acid (EPA) and docosahexaenoic acid (DHA). As used herein, the term "fatty acid oil mixture" includes fatty acids, such as unsaturated (e.g., monounsaturated, polyunsaturated) or saturated fatty acids, as well as pharmaceutically-acceptable esters, free acids, mono-, di- and triglycerides, derivatives, conjugates, precursors, salts, and mixtures thereof. In some embodiments, the fatty acid oil mixture comprises fatty acids, such as omega-3 fatty acids, in a form chosen from ethyl ester and triglyceride. In other embodiments, the fatty acids of the fatty acid oil mixture are in free acid form.

As used herein, the term "omega-3 fatty acids" includes natural and synthetic omega-3 fatty acids, as well as pharmaceutically acceptable esters, free acids, triglycerides, derivatives, conjugates (see, e.g., Zaloga et al., U.S. Patent Application Publication No. 2004/0254357, and Horrobin et al., U.S. Pat. No. 6,245,811, each hereby incorporated by reference), precursors, salts, and mixtures thereof. Examples of omega-3 fatty acid oils include, but are not limited to, omega-3 polyunsaturated, long-chain fatty acids such as a eicosapentaenoic acid (EPA); docosahexaenoic acid (DHA); α-linolenic acid (ALA); heneicosapentaenoic acid (HPA); docosapentaenoic acid (DPA); eicosatetraenoic acid; and octadecatetraenoic acid; esters of omega-3 fatty acids with glycerol such as mono-, di- and triglycerides; and esters of the omega-3 fatty acids and a primary, secondary and/or tertiary alcohol, such as, for example, fatty acid methyl esters and fatty acid ethyl esters. Further for example, omega-3 fatty acid oils may be long-chain fatty acids, such as EPA and DHA, triglycerides (TG) thereof, ethyl esters (EE) thereof, and/or mixtures thereof. The omega-3 fatty acids, their esters, triglycerides, derivatives, conjugates, precursors, salts and/or mixtures thereof can be used in their pure form and/or as a component of an oil, for example, marine oils (e.g., fish oil and purified fish oil concentrates), microbial oils, and plant-based oils.

The fatty acids according to the present disclosure may be derived from animal oils and/or non-animal oils. In some embodiments of the present disclosure, the fatty acid oil mixture is derived from at least one oil chosen from marine oil, algae oil, plant-based oil, and microbial oil. Marine oils include, for example, fish oil, krill oil, and lipid composition derived from fish. Plant-based oils include, for example, flaxseed oil, canola oil, mustard seed oil, and soybean oil. Microbial oils include, for example, products by Martek. In at least one embodiment of the present disclosure, the fatty acid oil mixture is derived from a marine oil, such as a fish oil. In at least one embodiment, the marine oil is a purified fish oil, for example, a purified tuna oil.

In some embodiments of the present disclosure, the fatty acids, such as omega-3 fatty acids, of the fatty acid oil mixture are esterified, such as alkyl esters and further for example, ethyl esters. In other embodiments, the fatty acids are chosen from mono-, di-, and triglycerides.

In some embodiments, the fatty acid oil mixture is obtained by a transesterification of the body oil of a fat fish species coming from, for example, anchovy or tuna oil, and subsequent physico-chemical purification processes, including urea fractionation followed by molecular distillation. In some embodiments, the crude oil mixture may also be subjected to a stripping process for decreasing the amount of environmental pollutants and/or cholesterol before the transesterification.

In another embodiment, the fatty acid oil mixture is obtained by using supercritical $CO_2$ extraction or chromatography techniques, for example to up-concentrate primary EPA and DHA from fish oil concentrates.

The fatty acid oil mixture of the present disclosure comprises omega-3 fatty acids, such as EPA and DHA. Further for example, in some embodiments, the fatty acid oil mixture comprises EPA and DHA in a form chosen from ethyl ester and triglyceride. In other embodiments, the fatty acid oil mixture comprises EPA and DHA in free acid form.

The fatty acid oil mixture of the present disclosure may further comprise at least one fatty acid other than EPA and DHA. Examples of such fatty acids include, but are not limited to, omega-3 fatty acids other than EPA and DHA and omega-6 fatty acids. For example, in some embodiments of the present disclosure, the fatty acid oil mixture comprises at least one fatty acid other than EPA and DHA chosen from α-linolenic acid, heneicosapentaenoic acid, docosapentaenoic acid, eicosatetraenoic acid, and octadecatetraenoic acid, and combinations thereof.

Examples of further fatty acids and mixtures thereof encompassed by the present disclosure include the omega-3 fatty acids defined in the European Pharmacopoeia Omega-3 Ethyl Ester 90 and purified marine oils, for example, as defined in the European Pharmacopoeia Omega-3 Triglycerides, the European Pharmacopoeia Omega-3 acid Ethyl Esters 60, or the Fish oil rich in omega-3 acids monograph. In some embodiments, the at least one fatty acid other than EPA and DHA is in a form chosen from ethyl ester and triglyceride. In other embodiments, the at least one fatty acid other than EPA and DHA is in free acid form.

Commercial examples of fatty acid oil mixtures suitable for the present disclosure comprising different fatty acid mixtures (e.g., that can be in the form of triglycerides (TG), ethyl esters (EE), free fatty acid form (FA) and/or as phospholipids) include, but are not limited to: Incromega™ omega-3 marine oil concentrates such as Incromega™ E1070, Incromega™ TG7010 SR, Incromega™ E7010 SR, Incromega™ TG6015, Incromega™ EPA500TG SR, Incromega™ E400200 SR, Incromega™ E4010, Incromega™ DHA700TG SR, Incromega™ DHA700E SR, Incromega™ DHA500TG SR, Incromega™ TG3322 SR, Incromega™ E3322 SR, Incromega™ TG3322, Incromega™ E3322, Incromega™ Trio TG/EE (Croda International PLC, Yorkshire, England); EPAX6000FA, EPAX5000TG, EPAX4510TG, EPAX2050TG, EPAX7010EE, EPAX5500EE, EPAX5500TG, EPAX5000EE, EPAX5000TG, EPAX6000EE, EPAX6000TG, EPAX6000FA, EPAX6500EE, EPAX6500TG, EPAX4510TG, EPAX1050TG, EPAX2050TG, EPAX 7010TG, EPAX7010EE, EPAX6015TG/EE, EPAX4020TG, and EPAX4020EE; Omacor®/Lovaza™/Zodin®/Seacor® finished pharmaceutical product, K85EE, and AGP 103 (Pronova BioPharma Norge AS); MEG-3® EPA/DHA fish oil concentrates (Ocean Nutrition Canada); DHA FNO "Functional Nutritional Oil" and DHA CL "Clear Liquid" (Lonza); Superba™ Krill Oil (Aker); omega-3 products comprising DHA produced by Martek; Neptune krill oil (Neptune); cod-liver oil products and anti-reflux fish oil concentrate (TG) produced by Møllers; Lysi Omega-3 Fish oil; Seven Seas Triomega® Cod Liver Oil Blend (Seven Seas); Fri Flyt Omega-3 (Vesterålens); Epadel (Mochida); AMR101 (Amarin); and Epanova™ (Omthera Pharmaceuticals); Pronova PURE products such as 200:500, 300:500, 240:600, 10:70, 10:70 EE/TG, 70:10 EE/TG, 50:30, 500:200 EE/TG, 400:200 EE/TG, 360:240 EE/TG, and 150:600 EE/TG, produced by Pronova; Epadel™ by Mochida; and Omthera products such as 44-55 mg/g EPA-FFA and 15-25 mg/g DHA-FFA, Amarin; >97% EPA-EE no DHA-EE, or >97w % EPA-EE and 0.5-4 mg/g; and MAXOMEGA and OMIVITAL produced by BASF. K85EE comprises about 430-495 mg/g EPA ethyl ester and about 347-403 mg/g DHA ethyl ester and at least about 800 mg/g omega-3 fatty acids.

In some embodiments of the compositions of the present disclosure, the weight ratio of EPA:DHA of the fatty acid oil mixture ranges from about 1:10 to about 10:1, from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1.

In at least one embodiment of the compositions disclosed herein, the concentration by weight of DHA is higher than the concentration by weight of EPA in the fatty acid oil mixture.

In one embodiment, the EPA:DHA weight ratio of the fatty acid oil mixture ranges from about 2:5 to about 3:5.

In another embodiment, the fatty acid oil mixture comprises >95% DHA in free fatty acid or ethyl ester form.

In yet another embodiment, the fatty acid oil mixture comprises >95% EPA in free fatty acid or ethyl ester form.

In still another embodiment, DHA is the predominant fatty acid in the composition disclosed herein.

In another embodiment, the fatty acid oil mixture comprises about 95% DHA but no EPA.

In at least one embodiment, the fatty acid oil mixture comprises >50% DHA.

In at least one embodiment, the fatty acid oil mixture comprises a weight ratio of EPA:DHA of 1.2:1 (430-495 mg/g EPA:347-403 mg/g DHA) and a total amount of omega-3 fatty acid ethyl esters of 800 mg/g.

The compositions presently disclosed may further comprise at least one antioxidant. Examples of antioxidants suitable for the present disclosure include, but are not limited to, α-tocopherol (vitamin E), calcium disodium EDTA, alpha tocoferyl acetates, butylhydroxytoluenes (BHT), and butylhydroxyanisoles (BHA). Other examples of antioxidants include ascorbic acid and pharmaceutically acceptable salts thereof such as sodium ascorbate, pharmaceutically acceptable esters of ascorbic acid including fatty acid ester conjugates, propyl gallate, citric acid and pharmaceutically acceptable salts thereof, malic acid and pharmaceutically acceptable salts thereof, and sulfite salts such as sodium sulfite and mixtures thereof.

Pharmaceutical Compositions

In some embodiments of the present disclosure, the fatty acid oil mixture acts as an active pharmaceutical ingredient (API). In some embodiments, the fatty acid oil mixture is present in a pharmaceutically-acceptable amount.

Where the composition is a pharmaceutical composition, the fatty acid oil mixture comprises at least 75% of at least one fatty acid chosen from EPA and DHA by weight of the fatty acid oil mixture. For example, in one embodiment, the fatty acid oil mixture comprises at least 80% of at least one fatty acid chosen from EPA and DHA by weight of the fatty acid oil mixture, such as at least 85%, at least 90%, or at least 95%, by weight of the fatty acid oil mixture.

For example, in some embodiments, the fatty acid oil mixture comprises from about 75% to about 95% of at least one fatty acid chosen from EPA and DHA by weight of the fatty acid oil mixture, such as from about 75% to about 90%, from about 75% to about 88%, from about 75% to about 85%, from about 75% to about 80%, from about 80% to about 97%, from about 80% to about 90%, from about 80% to about 85%, from about 85% to about 95%, from about 85% to about 90%, and further for example, from about 90% to about 95% of at least one fatty acid chosen from EPA and DHA, by weight of the fatty acid oil mixture, or any number in between. In at least one embodiment, the fatty acid oil mixture comprises from about 80% to about 90% of at least one fatty acid chosen from EPA and DHA, such as about 84%, by weight of the fatty acid oil mixture.

In at least one embodiment, the fatty acid oil mixture comprises about 80-130 mg/g EPA ethyl ester or triglyceride, and about 650-750 mg/g DHA ethyl ester or triglyceride. Further, the fatty acid oil mixture comprises from about 750 mg/g to about 900 mg/g omega-3 fatty acids.

In some embodiments, the fatty acid oil mixture comprises at least 95% of EPA or DHA, or EPA and DHA, by weight of the fatty acid oil mixture.

In a further embodiment, the fatty acid oil mixture may comprise other omega-3 fatty acids. For example, the present disclosure encompasses at least 90% omega-3 fatty acids, by weight of the fatty acid oil mixture.

In one embodiment, for example, the fatty acid oil mixture comprises from about 75% to about 90% EPA and DHA, by weight of the fatty acid oil mixture, wherein the fatty acid oil mixture comprises at least 90% of omega-3 fatty acids, by weight of the fatty acid oil mixture.

In one embodiment, the fatty acid oil mixture may comprise K85EE or AGP 103 (Pronova BioPharma Norge AS). In yet another embodiment, the fatty acid oil mixture may comprise K85FA (BioPharma Norge AS). For example, the fatty acid oil mixture comprises 430-495 mg/g EPA ethyl ester, 347-403 mg/g DHA ethyl ester, and at least 800 mg/g omega-3 fatty acids, relative to the fatty acid oil mixture.

In at least one embodiment, the fatty acid oil mixture comprises at least 75% of at least one fatty acid chosen from EPA and DHA by weight of the fatty acid oil mixture, of which at least 95% is EPA. In another embodiment, the fatty acid oil mixture comprises at least 80% of at least one fatty acid chosen from EPA and DHA by weight of the fatty acid oil mixture, of which at least 95% is EPA. In yet another embodiment, the fatty acid oil mixture comprises at least 90% of at least one fatty acid chosen from EPA and DHA by weight of the fatty acid oil mixture, of which at least 95% is EPA.

In another embodiment, the fatty acid oil mixture comprises at least 75% of at least one fatty acid chosen from EPA and DHA by weight of the fatty acid oil mixture, of which at least 95% is DHA. For example, in one embodiment, the fatty acid oil mixture comprises at least 80% of at least one fatty acid chosen from EPA and DHA by weight of the fatty acid oil mixture, of which at least 95% is DHA. In another embodiment, the fatty acid oil mixture comprises at least 90% of at least one fatty acid chosen from EPA and DHA by weight of the fatty acid oil mixture, of which at least 95% is DHA.

In at least one embodiment, the weight ratio of EPA:DHA of the fatty acid oil mixture ranges from about 1:2 to about 2:1. In at least one embodiment, the weight ratio of EPA:DHA of the fatty acid oil mixture ranges from about 1:1 to about 2:1.

In at least one embodiment, the pharmaceutical composition comprises a first composition comprising the fatty acid oil mixture and a second composition comprising the vitamin D.

In another embodiment, the pharmaceutical composition comprises a single composition comprising the fatty acid oil mixture and the vitamin D.

Food Supplement or Nutritional Supplement Compositions

The present disclosure further provides food supplement, pharmaceutical grade supplement, dietary supplement, over the counter (OTC) supplement, medical food, or nutritional supplement compositions comprising a fatty acid oil mixture, wherein the fatty acid oil mixture comprises 25% to 100% of at least one fatty acid chosen from EPA and DHA by weight of the fatty acid oil mixture.

In some embodiments, for example, the fatty acid oil mixture comprises less than 85% of at least one fatty acid chosen from EPA and DHA by weight of the fatty acid oil mixture, such as less than 65%, less than 60%, less than 55%, or less than 50%, by weight of the fatty acid oil mixture.

In some embodiments, the fatty acid oil mixture comprises from about 25% to about 90% of at least one fatty acid chosen from EPA and DHA, from about 45% to about 85% of at least one fatty acid chosen from EPA and DHA, by weight of the fatty acid oil mixture, from about 40% to about 80% of at least one fatty acid chosen from EPA and DHA, by weight of the fatty acid oil mixture, from about 40% to about 75% of at least one fatty acid chosen from EPA and DHA, by weight of the fatty acid oil mixture, from about 40% to about 70% of at least one fatty acid chosen from EPA and DHA, by weight of the fatty acid oil mixture, from about 40% to about 65% of at least one fatty acid chosen from EPA and DHA, by weight of the fatty acid oil mixture, or from about 50% to about 55% of at least one fatty acid chosen from EPA and DHA, by weight of the fatty acid oil mixture.

In at least one embodiment, the fatty acid oil mixture comprises from about 75% to about 85% of at least one fatty acid chosen from EPA and DHA, by weight of the fatty acid oil mixture.

In at least one other embodiment, the fatty acid oil mixture comprises from about 60% to about 75% of at least one fatty acid chosen from EPA and DHA, by weight of the fatty acid oil mixture.

In at least one embodiment, the fatty acid oil mixture comprises from about 25% to about 75% of at least one fatty acid chosen from EPA and DHA of the fatty acid oil mixture, of which at least 95% is EPA.

In at least one embodiment, the fatty acid oil mixture comprises from about 25% to about 75% of at least one fatty acid chosen from EPA and DHA of the fatty acid oil mixture, of which at least 95% is DHA.

In at least one embodiment, the fatty acid oil mixture comprises EPA and DHA present at a EPA:DHA weight ratio ranging from about 1:10 to about 1:5. In at least one other embodiment, the EPA:DHA weight ratio of the fatty acid oil mixture is about 1:7.

In some embodiments, the fatty acid oil mixture comprises >95% DHA in free fatty acid or ethyl ester form. In yet another embodiment, the fatty acid oil mixture comprises >95% EPA in free fatty acid or ethyl ester form.

In at least one embodiment, the fatty acid oil mixture comprises about 80-130 mg/g EPA ethyl ester or triglyceride, and about 650-750 mg/g DHA ethyl ester or triglyceride. Further, the fatty acid oil mixture comprises from about 750 mg/g to about 900 mg/g omega-3 fatty acids.

In at least one embodiment, the food supplement, nutritional supplement, or pharmaceutical grade supplement composition comprises a first composition comprising the fatty acid oil mixture and a second composition comprising the vitamin D.

In another embodiment, the food supplement, nutritional supplement, or pharmaceutical grade supplement composition comprises a single composition comprising the fatty acid oil mixture and the vitamin D.

Vitamin D

Vitamin D, or calciferol, is the general name for a collection of steroid-like substances including vitamin $D_2$ (ergocalciferol) and vitamin $D_3$ (cholecalciferol). The latter is the naturally occurring form used for low dose supplementation.

The term "vitamin D" used herein, means vitamin $D_3$. Vitamin $D_3$ is a secosteroid. The IUPAC name is (3β,5Z,7E)-9,10-secocholesta-5,7,10(19)-trien-3-ol. Another name is activated 7-dehydrocholesterol. The chemical structure of vitamin $D_3$ is as follows:

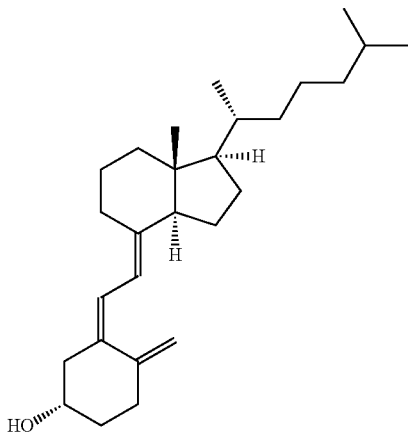 [SMILES: C=C1CC[C@H](O)C/C1=C/C=C1\CCC[C@]2(C)[C@@H]([C@H](C)CCCC(C)C)CC[C@@H]12]

Vitamin $D_3$ is metabolised by the liver to $25(OH)D_3$ (also known as 25-hydroxycholecalciferol, calcifediol, or calcidiol), which is then converted by the kidneys to $1,25(OH)_2D_3$ (also known as 1,25-dihydroxycholecalciferol, calcitriol, or active vitamin D hormone). $25(OH)D_3$, the major circulating form, has some metabolic activity, but $1,25(OH)_2D_3$ is the most metabolically active.

The chemical structure of $25(OH)D_3$ is as follows:

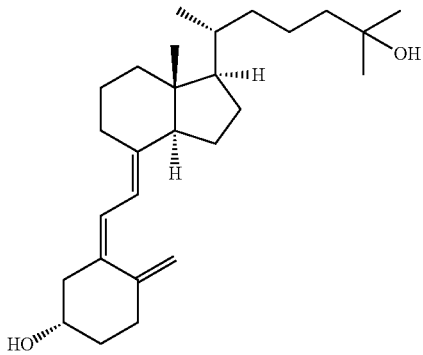 [SMILES: C=C1CC[C@H](O)C/C1=C/C=C1\CCC[C@]2(C)[C@@H]([C@H](C)CCCC(C)(C)O)CC[C@@H]12]

The chemical structure of $1,25(OH)_2D_3$ is as follows:

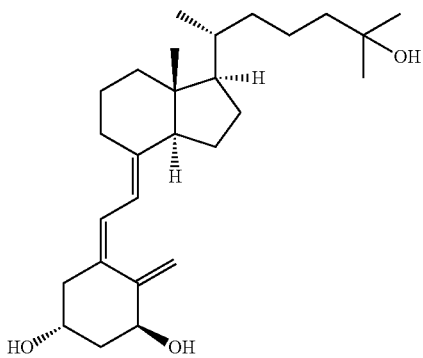 [SMILES: C=C1/C(=C\C=C2/CCC[C@]3(C)[C@@H]([C@H](C)CCCC(C)(C)O)CC[C@@H]23)C[C@@H](O)C[C@@H]1O]

The daily dose of Vitamin $D_3$ will for example be 2000-4000 International Units (IU) or 50-100 µg optionally divided into 2-4 capsules or tablets or any other formulation of the omega-3 fatty acid composition.

Forms

The compositions presently disclosed may be administered, e.g., in capsule, tablet, sachet, or any other form suitable for drug delivery. For example, the compositions may be in the form of a gelatin, or alginate capsule, a "cap-in-cap" capsule, a sachet, or a tablet. By way of example, the compositions may be in the form of a capsules made from gelatin, such as gelatin from marine and/or mammalian sources. Examples of such gelatins may be gelatin from fish, porcine and bovine sources. Likewise the gelatin may be chosen from type A gelatin, type B gelatin and a combination thereof. An example may be gelatin comprising type A porcine gelatin (e.g., pig bone, pig skin).

An example of a "cap-in-cap" capsule is DuoCap™, the only patented dual capsule system available to the pharmaceutical and nutraceutical industry. DuoCap involves specialist liquid-filling techniques using custom-designed filling equipment that allows the insertion of a pre-filled, smaller capsule into a larger, liquid-filled capsule. The smaller, inner capsule may contain either a liquid or semi-solid formulation and, according to the formulation or product requirements, either or both capsules may be of gelatin or HPMC composition and can be coated, if necessary. DuoCap™ has been successfully commercialised by Encap and is suited for both pharmaceutical and nutraceutical use.

The dosage form can be of any shape suitable for oral administration, such as spherical, oval, ellipsoidal, cube-shaped, regular, and/or irregular shaped. The dosage forms can be prepared according to processes known in the art and can include one or more additional pharmaceutically-acceptable excipients.

Gelatin Capsule or Tablet

In some embodiments of the present disclosure, the compositions are in a capsule or a tablet form. The capsule wall-forming material may comprise, for example, gelatin or polysaccharides other than alginate. In at least one embodiment, the capsule is a gelatin capsule. The capsules may be hard capsules or soft capsules.

When the dosage form is in the form of tablets, the tablets may be, for example, disintegrating tablets, fast dissolving tablets, effervescent tablets, fast melt tablets, and/or minitablets. Tablet formulations are described, for example, in patent publication WO 2006/000229. In some embodiments of the present disclosure, the tablets comprise Neusilin (e.g., magnesium aluminometasilicate).

When the capsule is a gelatin capsule, the gelatin may be chosen from type A gelatin, type B gelatin, or mixtures thereof. Gelatin is produced by destruction of secondary and, to a certain extent, higher structures in collagen (Babel, 1996). Gelatins may be of type A or B, depending on the kind of pre-treatment to which the collagenous tissue has been subjected. There are several processes by which collagen is processed to gelatin, but the two most common, as noted above, are the acidic and alkaline pre-treatments followed by extractions. Type A gelatin is obtained from animal skin, usually porcine skin, or hide, or from bovine, pork, and other animals, pre-treated with acid. The raw material is left in an acid soak for 10-30 hours depending on the nature of the collagenous stock. Type B gelatin is derived from collagenous raw materials subjected to alkaline pre-treatment. The alkali process is mainly used on bovine hide and bone collagfen sources where the animal is relatively old at slaughter (FRANCIS, F. J. 1999. Gelatin. *Wiley Encyclopedia of Food Science and Technology*. $2^{nd}$ ed.: John Wiley & Sons). The collagenous stock is left in liming pits for periods of 3-10 weeks depending on the nature of the stock and the ambient temperature.

The capsules and/or tablets of the present disclosure may comprise at least one coating. Such coatings can delay the release of the capsule or tablet (e.g., release of the at least one fatty acid chosen from EPA and DHA) for a predetermined period. For example, the at least one coating may allow the dosage form to pass through the stomach without being subjected to stomach acid or digestive juices to provide for delayed release of the at least one fatty acid chosen from EPA and DHA outside of the stomach. In some embodiments, the capsules and/or tablets release less than 30% of the total at least one fatty acid chosen from EPA and DHA in the stomach, such as less than 25%, less than 20%, less than 15%, or less than 10%.

In some embodiments, the at least one coating is chosen from enteric coatings, sub-layers, top-layers, and combinations thereof. The term "sub-layer" as used herein means a coating layer located between the capsule wall material (e.g., gelatin wall) or the tablet surface and an enteric coating. The term "top-layer" as used herein means a coating layer over an enteric coating covering the capsule wall material or the tablet surface. The chemical composition of sub-layers and top-layers may vary depending upon the overall composition of the capsule or tablet. Typical materials for the sub-layers and top-layers presently disclosed include film-forming agents such as polysaccharides, for example hydroxypropyl methyl cellulose.

In embodiments of the present disclosure, the capsules and/or tablets comprise at least one enteric coating. In some embodiments, the capsules and/or tablets comprise at least one enteric coating and at least one top-layer over the at least one enteric coating. In other embodiments, the capsules and/or tablets comprise at least one enteric coating and at least one sub-layer between the capsule wall or the tablet surface and the at least one enteric coating. In still other embodiments, the capsules and/or tablets comprise at least one enteric coating, at least one sub-layer between the capsule wall or the tablet surface, and at least one top-layer over the at least one enteric coating. In some embodiments, at least one of the sub-layer(s) and/or top-layer(s) comprises hydroxypropyl methyl cellulose.

In some embodiments, the at least one sub-layer comprises a sealant. Suitable sealants may comprise, for example, permeable or soluble agents such as hydroxypropyl methyl cellulose, hydroxypropyl cellulose, hydroxypropyl ethylcellulose, and xanthan gum. Other agents can be added to improve the processability of the sealant or barrier layer. Such agents include talc, colloidal silica, polyvinyl alcohol, titanium dioxide, micronized silica, fumed silica, glycerol monostearate, magnesium trisilicate and magnesium stearate, or a mixture thereof. The sealant or barrier layer can be applied from solution (e.g., aqueous) or suspension using any known means, such as a fluidized bed coater (e.g., Wurster coating) or pan coating system. Suitable sealants or barriers include, for example, Opadry® products such as Opadry® II available from Colorcon.

In some embodiments, the at least one coating is pH-independent. Coatings with pH-independent profiles generally erode or dissolve away after a predetermined period, and the period is generally directly proportional to the thickness of the coating. In other embodiments, the at least one coating is pH-dependent. Coatings with pH-dependent profiles can generally maintain their integrity while in the acid pH of the stomach, but erode or dissolve upon entering the more basic upper intestine. In some embodiments, the at least one coating is insoluble at a pH below about 5 and soluble at a pH above about 6.

Examples of coating materials suitable for the present disclosure include, but are not limited to, gelatin, film-forming agents, polymers, and copolymers. Examples of polymers and copolymers include, but are not limited to, acrylate-based polymers and copolymers (e.g., methacrylic acid, copolymers between methacrylic acid and methyl methacrylate, copolymers between methacrylic acid and methyl acrylate, copolymers between metacrylic acid and ethyl methacrylate, and copolymers between metacrylic acid and ethyl acrylate) and polysaccharide and/or cellulose-based polymers and copolymers (e.g., cellulose acetate phthalate, hydroxypropyl methyl cellulose phthalate, and hydroxypropyl methyl cellulose acetate succinate). Others polymers include, for example, polyvinyl acetate phthalate. Additional materials suitable for the at least one coating include pharmaceutically acceptable acidic compounds that may not dissolve at the low pl-1 in the stomach, but may dissolve at higher pH in the lower part of the gastrointestinal system.

Commerically-available examples of polymers suitable for the present disclosure include EUDRAGIT® products from Evonik. EUDRAGIT® polymers are polymeric lacquer substances based on acrylates and/or methacrylates, and may be pH-independent or pH-dependent.

For example, EUDRAGIT® RL and EUDRAGIT® RS are acrylic resins comprising copolymers of acrylic and methacrylic acid esters with a low content of quaternary ammonium groups. The ammonium groups are present as salts and give rise to permeability of the lacquer films. EUDRAGIT® RL and EUDRAGIT® RS are freely permeable (RL) and slightly permeable (RS), respectively, independent of pH. The polymers swell in water and digestive juices, in a pH-independent manner. In the swollen state, they are permeable to water and to dissolved active compounds. Specific examples include EUDRAGIT® RL 30D, EUDRAGIT® RL PO, EUDRAGIT® RL 100, EUDRAGIT® RL 12.5, EUDRAGIT® RS 30D, EUDRAGIT® RS PO, EUDRAGIT® RS 100, and EUDRAGIT® RS 12.5. Additional examples of pH-independent polymers include EUDRAGIT® E 100, EUDRAGIT® E 12.5, and EUDRAGIT® E PO. In at least one embodiment of the present disclosure, the at least one coating comprises EUDRAGIT® RS 30D.

Further, for example, EUDRAGIT® L and EUDRAGIT® S are anionic polymers synthesized from methacrylic acid and methacrylic acid methyl ester. They are insoluble in acids and pure water, and become soluble in neutral to weakly alkaline conditions. The permeability of EUDRAGIT® L and EUDRAGIT S is pH dependent. Above pH 5.0, the polymers become increasingly permeable. Specific examples include EUDRAGIT® L100-55, EUDRAGIT® L30D-55, EUDRAGIT® L100, EUDRAGIT® L100 12.5, EUDRAGIT® S100, EUDRAGIT® S12.5, and EUDRAGIT® FS 30D. Additional examples of pH-dependent polymers include EUDRAGIT® E100, EUDRAGIT® E 12.5, and EUDRAGIT® PO. In at least one embodiment of the present disclosure, the at least one coating comprises EUDRAGIT® L100-55.

The at least one coating may comprise at least one plasticizer. Plasticizers may, for example to improve the mechanical properties of pH-sensitive materials of the at least one coating. Suitable plasticizers include, but are not limited to, triethyl citrate, triacetin, polyethylene glycols, propylene glycol, phthalates, sorbitol and glycerin. The amount of plasticizer may vary depending upon the chemical composition of the at least one coating and the chemical composition and size of the capsule or tablet. In some embodiments, for example, the amount of plasticizer ranges from about 10% to about 60% by weight of the at least one coating.

The amount of coating material or thickness of the at least one coating may vary depending upon the chemical compositions and number of different coating layers, and chemical composition, size, and shape of the capsule or the tablet. Generally speaking, the coating should be sufficient thick to prevent substantial release of the at least one fatty acid chosen from EPA and DHA in the stomach, but also not contribute significantly to the capsule or tablet size. In some embodiments of the present disclosure, the thickness of the at least one coating ranges from about 10 microns to about 2 mm, such as from about 20 microns to about 1 mm. In some embodiments, the at least one coating comprises from about 1% to about 50% of the dry capsule wall-forming material (e.g., gelatin).

The capsules according to the present disclosure may be manufactured in low oxygen conditions to inhibit oxidation during the manufacturing process. The capsules may be prepared, for example, by direct encapsulation using standard methods known in the art. Examples of such methods include, but are not limited to, simple coacervation methods (see, e.g., ES 2009346, EP 0052510, and EP 0346879), complex coacervation methods (see, e.g., GB 1393805), double emulsion methods (see, e.g., U.S. Pat. No. 4,652, 441), simple emulsion methods (see, e.g., U.S. Pat. No. 5,445,832), and solvent evaporation methods (see, e.g., GB 2209937). Those methods may, for example, provide for continuous processing and flexibility of batch size. The present disclosure further provides for coating pre-prepared capsules (e.g., gelatin capsules comprising a fatty acid oil mixture). The coating of pre-prepared capsules may be performed, for example, by spraying such as using spray drying techniques or spraying into a coating pan comprising preformed capsules, or by dipping capsules into coating solutions.

In some embodiments of the present disclosure, the gelatin capsule fill content ranges from about 0.400 g to about 1.600 g. For example, in some embodiments, the capsule fill content ranges from about 0.400 g to about 1.300 g, or from about 0.600 g to about 1.200 g.

Alginate Capsule

In at least one embodiment, the compositions disclosed herein are in the form of a seamless capsule comprising a polysaccharide gel membrane outer surface shell comprising at least one alginate. In at least one embodiment, the polysaccharide gel membrane outer surface shell comprising at least one alginate encapsulates at least one emulsion comprises at least one oily phase, the at least one oily phase comprises the fatty acid oil mixture and at least one surfactant, the fatty acid oil mixture comprises at least 50% by weight of the emulsion, and the emulsion does not comprise marmelo mucilage.

As used herein, "alginate" includes alginic acid and/or pharmaceutically acceptable salts thereof, and refers generally to a copolymer comprising (1-4)-linked $\beta$-D-mannuronate (M) and its C-5 epimer $\alpha$-L-guluronate (G) residues. Non-limiting examples of alginate salts suitable for the disclosure herein include alginate salts of calcium, strontium, barium, or aluminum. In one embodiment, alginate comprises all or in part M-alginate. In another embodiment, alginate comprises all or in part G-alginate. In another embodiment, alginate comprises a combination of M-alginate and G-alginate. In at least one embodiment, the alginate has a G content of at least 30% by weight. In other embodiments, the alginate has a content ranging from about 40% to about 80% by weight.

In at least one embodiment, the alginate shell achieves a time-release delivery of the at least one fatty acid chosen from EPA and DHA upon administration to a subject.

In some embodiments of the present disclosure, the alginate shell further comprises coloring agents, stabilizers, sweetening agents, plasticizers, and/or hardeners.

Other polymers contemplated as comprising the capsule shell include polyesters, polyacrylates, polycyanoacrylates, polysaccharides, polyethylene glycol, and mixtures thereof. Other polymers may include, for example, gelatin, carboxymethylcellulose alginates, carrageenans, pectins, ethyl cellulose hydroxypropyl methylcellulose, cellulose acetophthalate, hydroxypropyl methylcellulose phthalate, methylacrylicacid copolymers (Eudragit® L and S), dimethylaminoethylmethacrylate copolymers (Eudragit E), trimethylammoniumethylmethacrylate copolymers (e.g., Eudragit® RL and RS), polymers and copolymers of lactic and glycolic acids, and mixtures thereof. In one embodiment, the polymer comprises a plasticizer additive, such as, for example, but not limited to, triethyl citrate, butyl phthalate, and mixtures thereof. Other additives may optionally be incorporated to improve and/or facilitate the encapsulation process, such as, for example, fluidizing agents, such as talc.

The seamless capsules of the present disclosure may comprise at least one excipient. Thus, the at least one excipient may be chosen from, for example, colloidal silicon dioxide, crospovidone, lactose monohydrate, lecithin, microcrystalline cellulose, polyvinyl alcohol, povidone, sodium lauryl sulfate, sodium stearyl fumarate, talc, titanium dioxide, and xanthum gum.

Surfactants may be chosen from, for example, glycerol acetates and acetylated glycerol fatty acid esters, such as acetin, diacetin, triacetin, and/or mixtures thereof. Suitable acetylated glycerol fatty acid esters include, but are not limited to, acetylated monoglycerides, acetylated diglycerides, and/or mixtures thereof.

In addition, the surfactant may be chosen from glycerol fatty acid esters, such as, for example, those comprising a fatty acid component of about 6-22 carbon atoms. Glycerol fatty acid esters can be chosen from monoglycerides, diglycerides, triglycerides, and/or mixtures thereof. Suitable glycerol fatty acid esters include monoglycerides, diglycerides, medium chain triglycerides with fatty acids having about 6-12 carbons, and/or mixtures thereof. Capmul® MCM (medium chain mono- and di-glycerides) is an example.

The at least one surfactant may be chosen from propylene glycol esters. For example, propylene glycol esters include, but are not limited to, propylene carbonate, propylene glycol monoacetate, propylene glycol diacetate, propylene glycol fatty acid esters, acetylated propylene glycol fatty acid esters, propylene glycol fatty acid monoesters, propylene glycol fatty acid diesters, and mixtures thereof. Fatty acids may comprise, for example, about 6-22 carbon atoms. Examples of propylene glycol esters include, but are not limited to, propylene glycol monocaprylate (Capryol®), propylene glycol dicaprylate, propylene glycol dicaprate, propylene glycol dicaprylate/dicaprate, and mixtures thereof.

The at least one surfactant may be chosen from ethylene glycol esters, such as, for example, monoethylene glycol monoacetates, diethylene glycol esters, polyethylene glycol esters, and mixtures thereof. Additional examples include ethylene glycol monoacetates, ethylene glycol diacetates, ethylene glycol fatty acid monoesters, ethylene glycol fatty acid diesters, and mixtures thereof. In addition, the ethylene glycol esters may be chosen from polyethylene glycol fatty acid monoesters, polyethylene glycol fatty acid diesters, and mixtures thereof. Ethylene glycol esters may be obtained from the transesterification of polyethylene glycol and a triglyceride, a vegetable oil, and/or mixture thereof, and include, for example, those marketed as Labrafil® and Labrasol®. Polyoxyethylene-sorbitan-fatty acid esters (also called polysorbates), e.g., of from 4 to 25 alkylene moieties, for example monolauryl, trilauryl, palmityl, stearyl, and oleyl esters, including, for example, Tween®.

A group of suitable surfactants includes propylene glycol monocaprylate, mixtures of glycerol and polyethylene glycol esters of long fatty acids, polyethoxylated castor oils, nonylphenol ethoxylates (Tergitol®), glycerol esters, oleoyl macrogol glycerides, propylene glycol monolaurate, propylene glycol dicaprylate/dicaprate, polyethylene-polypropylene glycol copolymer, and polyoxyethylene sorbitan monooleate.

Hydrophilic solvents which may be used include, but are not limited to, alcohols, e.g., a water miscible alcohol such as absolute ethanol, and/or glycerol. Other alcohols include glycols, e.g., any glycol obtainable from an oxide such as ethylene oxide, e.g., 1,2-propylene glycol. Other non-limiting examples include polyols, e.g., a polyalkylene glycol, e.g., poly($C_{2-3}$)alkylene glycol. One non-limiting example is a polyethylene glycol. The hydrophilic component may comprise an N-alkylpyrollidone, such as, but not; limited to, N—($C_{1-4}$alkyl)pyrollidone, e.g., N-methylpyrollidone,tri ($C_{1-4}$alkyl)citrate, e.g., triethylcitrate, dimethylisosorbide, ($Csc13$) alkanoic acid, e.g., caprylic acid and/or propylene carbonate. The hydrophilic solvent may comprise a main or sole component, e.g., an alcohol, e.g., C1-4-alcohol, e.g., ethanol, or alternatively a cocomponent, e.g., which may be chosen from partial lower ethers or lower alkanols. Suitable partial ethers include, for example, Transcutol® (which has the formula C2Hs—[O—(CH2)2]2-0H), Glycofurol® (also known as tetrahydrofurfuryl alcohol polyethylene glycol ether), or lower alkanols such as ethanol, such as, for example, glycerol acetates and acetylated glycerol fatty acid esters.

In at least one embodiment of the present disclosure, the capsules are seamless and comprise a polysaccharide gel membrane outer surface shell, and optionally a coating on said gel membrane. The polysaccharide gel membrane may be ionic. In some embodiments, the seamless capsules encapsulate an oily phase comprising the fatty acid oil mixture, water, and at least one surfactant. In some embodiments, the oily phase is an emulsion, such as an oil-in-water emulsion, a water-in-oil emulsion, or a water-in-oil-in-water emulsion. According to some embodiments of the present disclosure, the fatty acid oil mixture is present in an amount of at least 50% by weight of the emulsion, such as at least 55%, at least 60%, at least 65%, at least 70%, at least 75%, at least 80%, at least 85%, or even at least 90% by weight of said emulsion. In at least some embodiments, the seamless capsules do not comprise marmelo mucilage.

In some embodiments, the polysaccharide gel membrane further comprises at least one secondary film former chosen from cellulose acetate phthalate, cellulose acetate succinate, methyl cellulose phthalate, ethylhydroxycellulose phthalate, polyvinylacetatephtalate, polyvinylbutyrate acetate, vinyl acetate-maleic anhydride copolymer, styrene-maleic monoester copolymer, methyl acrylate-methacrylic acid copolymer, methacrylate-methacrylic acid-octyl acrylate copolymer, propylene glycol alginate, polyvinyl alcohol, carrageenans, pectins, chitosans, guar gum, gum acacia, sodium carboxymethylcellulose, hydroxypropylmethyl cellulose, hydroxypropylcellulose, methylcellulose, starches, and maltodextrins.

In some embodiments of the present disclosure, the polysaccharide gel membrane comprising the seamless capsules is an ionic gel membrane comprising at least one of alginate, propylene glycol alginate, and pectin. Said at least one of alginate, propylene glycol alginate, and pectin may be present in the form of a pharmaceutically-acceptable salt, non-limiting examples of which include salts of calcium, strontium, barium, or aluminum. The ionic polysaccharide of the seamless capsules presently disclosed may comprise an alginate having a weight-average molecular weight ranging from about 20,000 Daltons to about 500,000 Daltons, such as from about 50,000 Daltons to about 500,000 Daltons, or about 100,000 Daltons to about 500,000 Daltons, or about 150,000 Daltons to about 500,000 Daltons, or about 150,000 Daltons to about 300,000 Daltons, or about 20,000 Daltons to about 200,000 Daltons, or from about 20,000 Daltons to about 100,000 Daltons, or from about 30,000 Daltons to about 80,000 Daltons, or from about 30,000 Daltons to about 60,000 Daltons, or even ranging from about 30,000 Daltons to about 40,000 Daltons. In some embodiments of the present disclosure, the ionic polysaccharide comprises a mixture of two alginate components, such as a mixture of (i) an alginate having a weight-average molecular weight ranging from about 30,000 Daltons to about 40,000 Daltons; and (ii) an alginate having a weight-average molecular weight ranging from about 150,000 Daltons to about 500,000 Daltons. In such embodiments, the ratio of (i) to (ii), (i):(ii), may range from about 0.1 to about 20, or about 1 to about 16.

The seamless capsules presently disclosed may be in a shape other than spherical. For example, in some embodiments of the present disclosure, the seamless capsules are oblong, oval, or cylindrical. The seamless capsules may be wet or dry.

The thickness of the polysaccharide gel film comprising the alginate shell of the seamless capsules presently disclosed may range from about 0.01 millimeter to about 50 millimeters. The polysaccharide gel film may be wet or dry. In some embodiments, the thickness of the polysaccharide gel film ranges from about 0.3 millimeters to about 4 millimeters. In some embodiments, the thickness of the polysaccharide gel film ranges from about 0.04 millimeters to about 0.5 millimeters.

The seamless capsules according to the present disclosure may have a wet capsule diameter ranging from about 0.5 millimeters to about 50 millimeters, such as about 1 millimeter to about 40 millimeters, wherein the gel membrane has a thickness ranging from about 0.1 millimeter to about 5 millimeters, such as about 0.3 millimeters to about 4 millimeters.

In some embodiments, the seamless capsule is dried, and the gel membrane is a dry polysaccharide gel film on the outer surface which constitutes up to 10% by weight of the dried seamless capsule. In some embodiments, the dry capsule has a diameter ranging from about 0.5 millimeters to about 35 millimeters, wherein the dry polysaccharide gel film has a thickness ranging from about 0.01 millimeters to about 5 millimeters. In some embodiments, the thickness of the dry polysaccharide gel film ranges from about 0.04 millimeters to about 0.5 millimeters.

According to at least one embodiment, an oil-in-water emulsion is encapsulated in seamless capsules for oral administration. The seamless capsules may also be known generally as softgels.

Seamless capsules of the present disclosure may be prepared, for example, by a method disclosed in WO 2003/084516, comprising: (a) preparing an emulsion comprising oil, water, an emulsifier, and at least one of a water-soluble monovalent metal salt, polyvalent metal salt, and an acid, wherein the oil is present in an amount of at least 50% by weight of the emulsion; and (b) adding at least one portion of the emulsion to an aqueous gelling bath comprised of at least one ionic polysaccharide, thereby encapsulating the at least one portion of the emulsion in a polysaccharide gel membrane, and optionally (c) drying the resulting capsules.

In one embodiment of the present disclosure, the at least one polyvalent metal salt is calcium chloride ($CaCl_2$) and the at least one ionic polysaccharide is alginate. In one embodiment, the alginate is all or in part M-alginate. In one embodiment, the alginate is all or in part G-alginate. In one embodiment, the alginate is a mixture of M-alginate and G-alginate.

Vitamin D may be incorporated into the compositions, supplements and capsules disclosed herein in several ways. For example, vitamin D may be dissolved or suspended in the fatty acid oil mixture. In at least one embodiment, vitamin D comprises "beads"—small particles agglomerated together—in the fatty acid oil mixture. In another embodiment, vitamin D is encapsulated in tablets or capsules present in the fatty acid oil mixture which is itself contained in a capsule (sometimes called "cap-in-cap"). In yet another embodiment, vitamin D comprises a dispersion of nanoparticles in the fatty acid oil mixture.

As another way vitamin D may be incorporated into the compositions, supplements and capsules disclosed herein, vitamin D may be incorporated or partially incorporated into the wall of the capsule containing the fatty acid oil mixture.

As yet another option, vitamin D may be present in or on the coating of the capsule containing the fatty acid oil mixture. In one such embodiment, vitamin D is sprayed onto the outside of the capsule containing the fatty acid oil mixture. In another such embodiment, vitamin D is present between two coatings on the outside of the capsule containing the fatty acid oil mixture.

Methods or Uses

The present disclosure further encompasses methods of at least one of preventing and treating psoriasis in a subject in need thereof. The pharmaceutical compositions presently disclosed may be administered, e.g., in capsule, tablet or any other suitable form for drug delivery, to a subject for at least one of preventing and treating psoriasis.

The total daily dosage of the fatty acid oil mixture may range in amount from about 1 g to about 6 g, from about 1 g to about 4 g, or from about 2 g to about 4 g. For example, in at least one embodiment, the total daily dosage of the fatty acid oil mixture ranges in amount from about 1.5 g to about 3 g. The total daily dosage of the vitamin D may range in amount from about 25 to about 150 µg or from about 1000 to about 6000 IU, from about 25 to about 100 µg, from about 25 to about 50 µg, from about 50 to about 100 µg, from about 50 to about 75 µg, or from about 75 to about 100 µg In one embodiment, the fatty acid oil mixture is chosen from K85EE and AGP 103 fatty acid oil compositions. In another embodiment, the fatty acid oil mixture comprises K85FA.

The present disclosure further encompasses methods of improving at least one parameter associated with psoriasis. The food supplement, nutritional supplement, or pharmaceutical grade supplement compositions presently disclosed may be administered, e.g., in capsule, tablet or any other suitable form for drug delivery, to a subject for at least one of decreasing skin flaking and itching associated with psoriasis and improving dry skin conditions, e.g., skin dryness, dry skin aspects, skin comfort, skin soothing, and/or signs of skin aging.

The total daily dosage of the fatty acid oil mixture may range in amount from about 1 g to about 2 g. For example, in at least one embodiment, the total daily dosage of the fatty acid oil mixture may range in amount from about 1.5 g to about 2 g. The total daily dosage of the vitamin D may range in amount from about 50 to about 100 µg.

In at least one embodiment, the pharmaceutical composition comprises a first composition comprising the fatty acid oil mixture and a second composition comprising the vitamin D, wherein the two compositions are administered to the subject in need thereof in any order, and wherein the first composition and the second composition can each be in the form of any of a gelatin or fish gelatin capsule or tablet, a sachet, or a seamless capsule comprising a polysaccharide gel membrane outer surface shell comprising at least one alginate.

In at least one embodiment, the food supplement, nutritional supplement, or pharmaceutical grade supplement composition comprises a first composition comprising the fatty acid oil mixture and a second composition comprising the vitamin D, wherein the two compositions are administered to the subject in need thereof in any order, and wherein the first composition and the second composition can each be in the form of any of a gelatin or fish gelatin capsule or tablet, a sachet, or a seamless capsule comprising a polysaccharide gel membrane outer surface shell comprising at least one alginate.

Formulations

In some embodiments of the present disclosure, the composition is a pharmaceutical composition in a gelatin capsule or a tablet form comprising a fatty acid oil mixture comprising at least 75% of at least one fatty acid chosen from eicosapentaenoic acid (EPA) and docosahexaenoic acid (DHA), by weight of the fatty acid oil mixture, wherein the EPA and DHA are in a form chosen from ethyl ester and triglyceride; and vitamin D, wherein the gelatin capsule or the tablet comprises at least one coating.

In other embodiments, the composition in a gelatin capsule or a tablet form is a food supplement, dietary supplement, nutritional supplement, OTC supplement, medical food, or pharmaceutical grade supplement composition comprising a fatty acid oil mixture comprising from about 25% to about 100% of at least one fatty acid chosen from eicosapentaenoic acid (EPA) and docosahexaenoic acid (DHA), by weight of the fatty acid oil mixture, wherein the EPA and DHA are in a form chosen from ethyl ester and triglyceride; and vitamin D, wherein the gelatin capsule or the tablet comprises at least one coating.

In one embodiment, the efficacious dose of oral omega-3/vitamin D combinations should range from 1 to 4 grams omega-3 and from 1000 to 4000 IU vitamin $D_3$.

The following examples are intended to illustrate the present disclosure without, however, being limiting in nature. It is understood that the skilled artisan will envision additional embodiments consistent with the disclosure provided herein.

EXAMPLES

Example 1

In an in vivo study the effects of 4-6 grams Omacor versus 4 grams placebo versus 4 grams Omacor+1000-4000 IU vitamin $D_3$ versus placebo+1000-4000 IU vitamin $D_3$ upon severity of psoriasis (PASI), VDR expression and expression of pro- and anti-inflammatory markers such as interleukin (IL)-8 and anti-IL-10 in skin biopsy will be evaluated.

Example 2

In an in vitro assays synergistic effects of various combinations of the PPAR ligands, eicosapentaenoic acid (EPA), docosahexaenoic acid (DHA) with the VDR ligand, 1,25 $(OH)_2D_3$, upon T-cell proliferation and mRNA levels of selected cytokines and growth factors will be evaluated A dose response curve of the effects of titrated concentrations of $1,25(OH)_2D_3$ (ranging from $10^{-12}$ to $10^{-6}$ M) will be established and subsequently tested in combination with either EPA or DHA, each present at 2, 5, 10, 15, 30 and 50 μM.

Example 3

In further in vivo studies, the effects of the following will be evaluated, wherein the dosage of the fatty acid oil mixture ranges from 1 to 4 gram and the content of vitamin D ranges from 2000 to 4000 (IU).

| Fatty acid oil mixture (w %) | EPA EE or TG content (w %) | DHA EE/TG content (w %) | Omega-3 (w %) | Vitamin D content (International Units (IU) $1.25(OH)_2D_3$) |
|---|---|---|---|---|
| Pronova DHA 1070EE | 8-13% | 65-75% | 75-90% | 2000-4000 |
| Pure DHA (>95% DHA-EE) | less than 5% | >95% DHA-EE | at least 95% | 2000-4000 |
| Ultra Pure DHA (>97% DHA-EE and no EPA) | no EPA | >97% DHA-EE | at least 97% | 2000-4000 |
| EPAX 10:50 or similar | 7-12% | 45-55% | at least 55% omega-3 | 2000-4000 |
| EPAX 20:50 or similar | 15-25 | 45-55% | at least 60% | 2000-4000 |
| Pronova 70:10 | 65-75 w % | 8-13 w % | 75-90% | 2000-4000 |

* EE = ethyl ester; TG = triglyceride

Example 4

In an in vivo study, the effects of 2 or 3 grams Pronova DHA 10:70 EE versus 2 or 3 grams placebo versus 2 or 3 grams Pronova DHA 10:70 EE+4000 IU vitamin $D_3$ versus placebo+4000 IU vitamin $D_3$ upon severity of psoriasis (PASI), VDR expression and expression of pro- and anti-inflammatory markers such as interleukin (IL)-8 and anti-IL-10 in skin biopsy will be evaluated.

Example 5

Examples of fatty acid oil mixtures which may be used in the compositions, methods, and uses disclosed herein include those listed in the following table:

| Fatty acid oil mixture | EPA EE or TG content (mg/g) | DHA EE or TG content (mg/g) | Total EPA and DHA (mg/g) | Vitamin D content (International Units (IU) $1.25(OH)_2D_3$) |
|---|---|---|---|---|
| PRONOVAPURE 150:600 | 125-175 mg/g | 575-625 mg/g | 700-800 mg/g | 2000-4000 |
| PRONOVAPURE 200:500 | Min 200 mg/g EPA-EE or EPA-TG | Minimum 500 mg/g EPA-EE or EPA-TG | Minimum 700 mg/g | 2000-4000 |
| PRONOVA PURE 360:240 | Minimum 360 mg/g | Minimum 240 mg/g | Minimum 700 mg/g | 2000-4000 |
| MAXOMEGA 600:300 | Minimum 600 mg/g | Minimum 300 mg/g | Mimimum 900 mg/g | 2000-4000 |
| MAXOMEGA high DHA | | Minimum 750 mg/g | | 2000-4000 |

What is claimed is:

1. A food supplement, dietary supplement, nutritional supplement, over the counter (OTC) supplement, medical food or pharmaceutical grade supplement composition for improvement of at least one parameter associated with psoriasis comprising:
   a fatty acid oil mixture comprising from about 25% to about 100% of at least one fatty acid chosen from eicosapentaenoic acid (EPA) and docosahexaenoic acid (DHA), by weight of the fatty acid oil mixture, wherein the fatty acid oil mixture comprises >50% DHA, and wherein the EPA and DHA are present at a EPA:DHA weight ratio ranging from about 1:10 to about 1:2, and further wherein the EPA and DHA are in a form chosen from ethyl ester, triglyceride, and free fatty acid; and
   vitamin D;
   wherein the improvement of at least one parameter associated with psoriasis is chosen from:
   decreasing skin flaking and skin itching associated with psoriasis; and
   improving dry skin conditions.

2. The composition according to claim 1, wherein the dry skin conditions are chosen from skin dryness, dry skin aspects, skin comfort, skin soothing, and signs of skin aging.

3. The composition according to claim 1, wherein the fatty acid oil mixture further comprises at least one other fatty acid other than EPA and DHA in a form chosen from ethyl ester and triglyceride.

4. The composition according to claim 1, wherein the fatty acid oil mixture is derived from at least one oil chosen from marine oil, algae oil, plant-based oil, and microbial oil.

5. The composition according to claim 1, further comprising at least one antioxidant.

6. The composition according to claim 1, wherein the composition is in the form of a gelatin or alginate capsule, a "cap-in-cap" capsule, a sachet, or a tablet.

7. The composition according to claim 1, wherein vitamin D is (3β,5Z,7E)-9,10-secocholesta-5,7,10(19)-trien-3-ol (vitamin D₃):

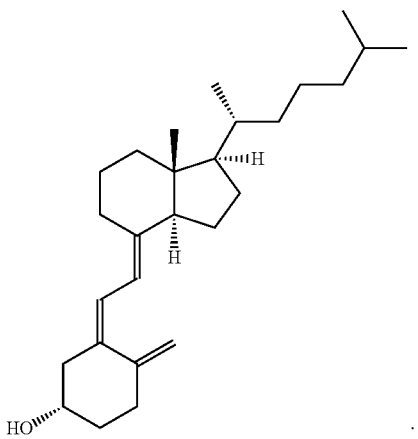 [SMILES: C=C1CC[C@H](O)C/C1=C/C=C1\CCC[C@]2(C)[C@@H]([C@H](C)CCCC(C)C)CC[C@@H]12]

8. The composition according to claim 1, wherein vitamin D is dissolved, partly dissolved, or suspended in the oil mixture.

9. The composition according to claim 1, wherein the vitamin D is suspended or dissolved in the fatty acid oil mixture, encapsulated or micro-encapsulated in the fatty acid oil mixture, sprayed on a capsule encapsulating the fatty acid oil mixture, or a cap-in-cap capsule.

10. A food supplement, dietary supplement, nutritional supplement, over the counter (OTC) supplement, medical food or pharmaceutical grade supplement composition for improvement of at least one parameter associated with psoriasis comprising:

a fatty acid oil mixture comprising from about 25% to about 100% of at least one fatty acid chosen from eicosapentaenoic acid (EPA) and docosahexaenoic acid (DHA), by weight of the fatty acid oil mixture, wherein the fatty acid oil mixture comprises >95% DHA, and wherein the EPA and DHA are in a form chosen from ethyl ester, triglyceride, and free fatty acid; and vitamin D;

wherein the improvement of at least one parameter associated with psoriasis is chosen from:

decreasing skin flaking and skin itching associated with psoriasis; and improving dry skin conditions.

11. The composition according to claim 1, wherein the EPA and DHA are present at a EPA:DHA weight ratio selected from about 1:2.5, about 1:4 and about 1:7.

* * * * *